United States Patent [19]

Kricka et al.

[11] Patent Number: 5,427,946

[45] Date of Patent: * Jun. 27, 1995

[54] MESOSCALE SPERM HANDLING DEVICES

[75] Inventors: Larry J. Kricka, Berwyn; Peter Wilding, Paoli, both of Pa.

[73] Assignee: Trustees of the University of Pennsylvania, Philadlephia, Pa.

[ * ] Notice: The portion of the term of this patent subsequent to Mar. 22, 2011 has been disclaimed.

[21] Appl. No.: 184,577

[22] Filed: Jan. 21, 1994

Related U.S. Application Data

[63] Continuation of Ser. No. 877,661, May 1, 1992, Pat. No. 5,296,375.

[51] Int. Cl.⁶ ............................................. C12M 1/34
[52] U.S. Cl. ..................................... 435/291; 422/58; 422/61; 435/7.2; 435/7.21; 435/259; 436/501; 436/524; 436/807; 436/809
[58] Field of Search .......................... 422/55–58, 422/61; 436/164, 524, 807, 809, 49, 501, 180; 435/7.21, 259, 291, 6, 7.2, 287

[56] References Cited

U.S. PATENT DOCUMENTS

| | | | |
|---|---|---|---|
| 3,799,742 | 3/1974 | Coleman | 422/61 |
| 3,906,929 | 9/1975 | Augspurger | 435/2 |
| 4,233,029 | 11/1980 | Columbus | 422/55 |
| 4,302,313 | 11/1981 | Columbus | 422/68 |
| 4,618,476 | 10/1986 | Columbus | 422/100 |
| 4,790,640 | 12/1988 | Nason | 350/534 |
| 4,906,439 | 3/1990 | Grenner | 422/56 |
| 4,908,112 | 3/1990 | Pace | 204/299 R |
| 4,911,782 | 3/1990 | Brown | 156/633 |
| 4,963,498 | 10/1990 | Hillman et al. | 436/69 |
| 5,135,720 | 8/1992 | Uchida | 435/291 X |
| 5,147,606 | 9/1992 | Charlton et al. | 422/56 |
| 5,296,375 | 3/1994 | Kricka et al. | 435/291 |

FOREIGN PATENT DOCUMENTS

| | | |
|---|---|---|
| 0320308 | 6/1989 | European Pat. Off. . |
| 0439182 | 7/1991 | European Pat. Off. . |
| 0439893 | 8/1993 | European Pat. Off. . |
| 3915920 | 11/1990 | Germany . |
| 2131972 | 6/1984 | United Kingdom . |
| 2191110 | 12/1987 | United Kingdom . |
| 220003 | 12/1989 | United Kingdom . |
| 9009596 | 8/1990 | WIPO . |
| WO91/13338 | 9/1991 | WIPO . |
| 9115750 | 10/1991 | WIPO . |
| 91/16966 | 11/1991 | WIPO . |

OTHER PUBLICATIONS

Anderson, *Nature*, 355:379 (1992).
Angell, et al., *Scientific American*, 248:44–55 (1983).
Appenzeller, *Science*, 254:1300–1342 (1991).

(List continued on next page.)

*Primary Examiner*—James C. Housel
*Assistant Examiner*—Maureen M. Wallenhorst
*Attorney, Agent, or Firm*—Dann, Dorfman, Herrell and Skillman

[57] ABSTRACT

Devices and methods are provided for the clinical analysis of a sperm sample. The devices include a solid substrate, typically on the order of a few millimeters thick and approximately 0.2 to 2.0 centimeters square, microfabricated to define a sample inlet port and a mesoscale flow channel extending from the inlet port. In one embodiment, a sperm sample is applied to the inlet port, and the competitive migration of the sperm sample through the mesoscale flow channel is detected to serve as an indicator of sperm motility. In another embodiment, the substrate of the device is microfabricated with a sperm inlet port, an egg nesting chamber, and an elongate mesoscale flow channel communicating between the egg nesting chamber and the inlet port. In this embodiment, a sperm sample is applied to the inlet port, and the sperm in the sample are permitted to competitively migrate from the inlet port through the channel to the egg nesting chamber, where in vitro fertilization occurs. The devices of the invention may be used in a wide range of applications in the analysis of a sperm sample, including the analysis of sperm morphology or motility, to assess sperm binding properties, and for in vitro fertilization.

2 Claims, 9 Drawing Sheets

OTHER PUBLICATIONS

Barany, *Proc. Natl. Acad. Sci,* 88:189∝192 (1991).
Brown, "Development of a Stopped-Flow Cytometer," NSF Grant No. ISI 87-60730.
Brunette, *Exper. Cell Res.,* 167:203-217 (1986).
Brunette, *Exper. Cell Res.,* 164:11-26 (1986).
Columbus et al., *Clin. Chem.,* 33:1531-1537 (1987).
DeLuca et al., *Arch. Biochem. Biophys.,* 255:285-292 (1983).
Dessy, *Chemometrics and Intelligent Laboratory Systems,* 8:311 (1990).
Esashi et al., "Integrated Flow Control Systems Fabricated on a Silicon Wafer," Proceedings, Electrochemical Society Conference, HI (18-23 Oct., 1987), Electrochemical Society, Pennington, N.J., pp. 31-38B, 1987.
Fromherz et al., *Biochimica et Biophysica Acta,* 1062:103-107 (1991).
Goin et al., *Clin. Chem.,* 32:1655-1659 (1986).
Haller in: *Solid Phase Biochemistry,* W. H. Scouten, Ed., John Wiley, New York, pp. 535-597 (1983).
Hanazato et al., *IEEE Transactions Electron. Devices;* ED33:47-51 (1986).
Hoopman, "Microchanneled Structures," *Applied Technology Laboratory,* 3M Center, St. Paul, Minn. 55144-1000.
Howe et al., *IEEE Transactions Electron Devices,* ED33:499-506 (1986).
Hung et al, *Med., & Biol. Engng.,* 9:237-245 (1971).
Jonsson, *Methods in Enzymology,* 137:381-389 (1988).
Kennedy et al., *Clin. Chem. Acta.,* 70:1-31 (1976).
Kenny et al., *Appl. Phys. Lett.,* 58:100-102 (1991).
Kikuchi et al., *Biorheology,* 26:1055 (1989), Abstract.
Kittilsland et al., *Journal de Physique,* 49 (C4):641-644 (1988).
Kittilsland et al., *Sensors and Activators,* A21-A23:904-907 (1990).
Kricka et al., *SPIE,* 1167:159-168 (1989).
Kricka et al., *Clin Chem.,* 26:741-744 (1980).
LaCelle, *Blood Cells,* 12:179-189 (1986).
Mandenius et al., *Anal. Biochem.,* 137:106-114 (1984).
Mandenius et al., *Anal. Biochem.,* 170:68-72 (1988).
Mandenius et al., *Methods in Enzymology,* 137:388-394 (1988).
Manz et al., *Trends in Anal. Chem.,* 10:144-149 (1991).
Masuda et al., Proc. *IEEE/IAS Meeting,* pp. 1549-1553 (1987).
McCartney et al., *Cancer Res.,* 41:3046-3051 (1981).
Moghissi et al., *Am. J. Obstet. Gynecol.,* 114:405-(1972).
Nakamura, *Immunochemical Assays and Biosensor Technology for the 1990's,* American Society of Microbiology, Washington, D.C., pp. 205-215 (1992).
Nakamura et al., *Anal. Chem.,* 63:268-272 (1991).
Parce et al., *Science,* 24:243-247 (1988).
Rosenberg et al., *Clin. Chem.,* 30:1462-1466 (1984).
Rosenberg et al., *Clin. Chem.,* 31:1444-1448 (1985).
Sankolli et al., *J. Imun. Methods,* 104:191-194 (1987).
Sato, et al., *Sensors and Actuators,* A21-A23:948-951 (1990).
Shoji, et al., *Sensors and Actuators,* 15:101-107 (1988).
Stange et al., *Biomaterials,* 9:3-6 (1988).
Van Lintel, *Sensors and Actuators,* 15:153-167 (1988).
Wallis et al., *J. Amer. Ceramic Soc.,* 53;563-567 (1970).
Wang et al., *In Service Training,* 10:9-15 (1992).
Washizu et al., *Proceedings IEEE/IAS Meeting,* pp. 1735-1740 (1988).
Weissman et al. *Am Inst. Chem. Eng. J.* 17:25-30 (1971).
*WHO Laboratory Manual,* Cambridge University Prep., 1987, pp. 1-2 and 64-67.
Wilding, *Advanced Hospital Technology Laboratory,* Oct., 1990 pp. 38-42.
Zemel et al. in: *Fundamentals and Applications of Chemical Sensors,* D. Schuetzle and R. Hammerle, Eds., *ACS Symposium Series 309,* Washington, D.C., 1986, p. 2.
Biotrack, Ciba Corning, May, 1989.
Roche, On-Trak ™, Sep., 1988.
Lopata et al., "A Method for Collecting Motile Spermatozoa From Human Semen," *Fertility and Sterility,* 27:677-684 (1976).
Ikuma et al., "Role of Sperm Passage Through Cervical Mucus Fertilizing Capacity Tested by In-Vitro Fertilization With Zona-Free Hamster Eggs," *Acta Obstet Gynaecol Jpn,* 41:167-172 (1989) (Abstract).

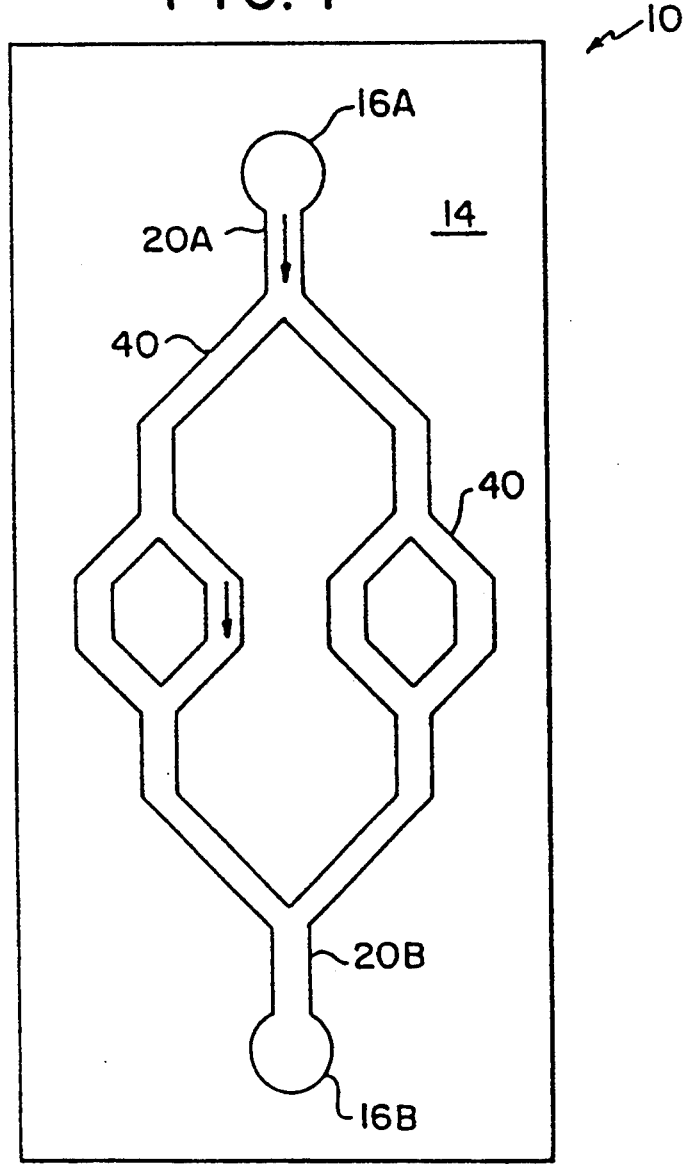

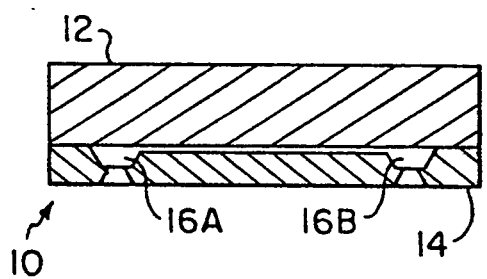
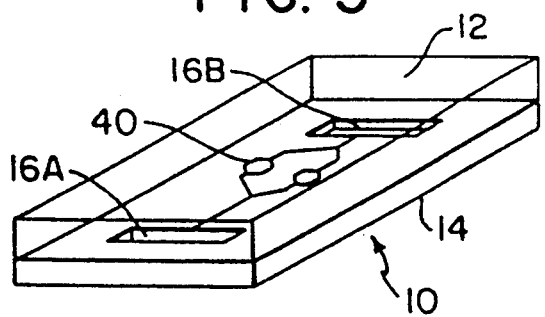
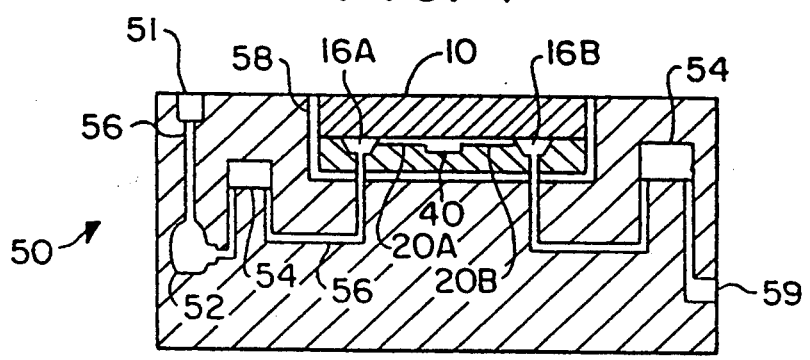

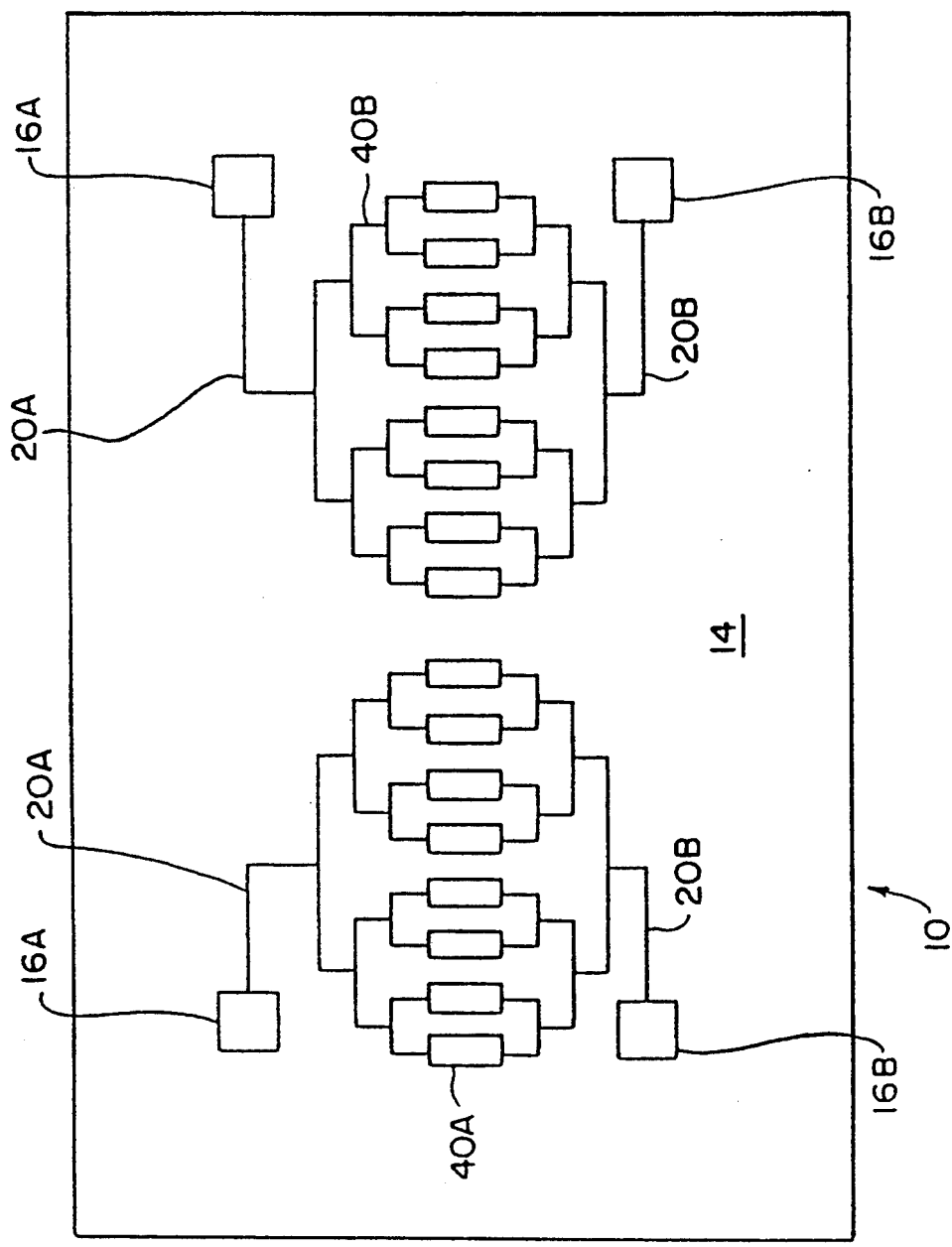

MESOSCALE SPERM HANDLING DEVICES

REFERENCE TO RELATED APPLICATIONS

This is a continuation of application Ser. No. 07/877,661 filed on May 1, 1992 now U.S. Pat. No. 5,296,375, issued Mar. 22, 1994.

This application is being filed contemporaneously with the following related applications: U.S. Ser. No. 07/877,702 filed May 1, 19972, now abandoned U.S. Ser. No. 07/877,701, filed May 1, 1992, now abandoned U.S. Ser. No. 07/877,536 filed May 1, 1992, and issued as U.S. Pat. No. 5,304,487 on Apr. 19, 1994 and U.S. Ser, No. 07/877,662, filed May, 1, 1992, now abandoned the disclosures of which are incorporated herein by reference.

BACKGROUND OF THE INVENTION

This invention relates generally to methods and apparatus for conducting analyses. More particularly, the invention relates to the design and construction of small, typically single-use, modules capable of rapidly analyzing microvolumes of a fluid sample.

In recent decades the art has developed a very large number of protocols, test kits, and cartridges for conducting analyses on biological samples for various diagnostic and monitoring purposes. Immunoassays, agglutination assays, and analyses based on polymerase chain reaction, various ligand-receptor interactions, and differential migration of species in a complex sample all have been used to determine the presence or concentration of various biological compounds or contaminants, or the presence of particular cell types.

Recently, small, disposable devices have been developed for handling biological samples and for conducting certain clinical tests. Shoji et al. reported the use of a miniature blood gas analyzer fabricated on a silicon wafer. Shoji et al., *Sensors and Actuators*, 15:101–107 (1988). Sato et al. reported a cell fusion technique using micromechanical silicon devices. Sato et al., *Sensors and Actuators*, A21–A23:948–953 (1990). Ciba Corning Diagnostics Corp. (USA) has manufactured a microprocessor-controlled laser photometer for detecting blood clotting.

Micromachining technology originated in the microelectronics industry. Angell et al., *Scientific American*, 248:44–55 (1983). Micromachining technology has enabled the manufacture of microengineered devices having structural elements with minimal dimensions ranging from tens of microns (the dimensions of biological cells) to nanometers (the dimensions of some biological macromolecules). This scale is referred to herein as "mesoscale". Most experiments involving mesoscale structures have involved studies of micromechanics, i.e., mechanical motion and flow properties. The potential capability of mesoscale structures has not been exploited fully in the life sciences.

Brunette (*Exper. Cell Res.*, 167:203–217 (1986) and 164:11–26 (1986) ) studied the behavior of fibroblasts and epithelial cells in grooves in silicon, titanium-coated polymers and the like. McCartney et al. (*Cancer Res.*, 41:3046–3051 (1981)) examined the behavior of tumor cells in grooved plastic substrates. LaCelle (*Blood Cells,* 12:179–189 (1986)) studied leukocyte and erythrocyte flow in microcapillaries to gain insight into microcirculation. Hung and Weissman reported a study of fluid dynamics in micromachined channels, but did not produce data associated with an analytic device. Hung et al., *Med. and Biol. Engineering,* 9:237–245 (1971); and Weissman et al., *Am. Inst. Chem. Eng. J.,* 17:25–30 (1971). Columbus et al. utilized a sandwich composed of two orthogonally orientated v-grooved embossed sheets in the control of capillary flow of biological fluids to discrete ion-selective electrodes in an experimental multi-channel test device. Columbus et al., *Clin. Chem.,* 33:1531–1537 (1987). Masuda et al. and Washizu et al. have reported the use of a fluid flow chamber for the manipulation of cells (e.g. cell fusion). Masuda et al., *Proceedings IEEE/IAS Meeting,* pp. 1549–1553 (1987); and Washizu et al., *Proceedings IEEE/IAS Meeting* pp. 1735–1740 (1988). The art has not fully explored the potential of using mesoscale devices for the analyses of biological fluids and detection of microorganisms.

The current analytical techniques utilized for the detection of microorganisms and cells are rarely automated, invariably employ visual and/or chemical methods to identify the strain or sub-species, and are inherently slow procedures. There is a need for convenient and rapid systems for clinical assays. There is particularly a growing need for standardized procedures for the analysis of semen, capable of providing reliable and rapid results, which may be used in the assessment of male infertility, and for a range of other applications including in vitro fertilization (IVF), artificial insemination by donor semen (AID) and forensic medicine. The World Health Organization, *WHO Laboratory Manual for the Examination of Human Semen and Semen-Cervical Mucus Interaction,* Cambridge University Press, Cambridge, U.K. (1987). The evaluation of male infertility through the analysis of semen involves a range of tests including the assessment of sperm count, motility, morphology, hormone levels, sperm antibodies, sperm cervical mucus interaction and sperm biochemistry. Wang et al., *American Association for Clinical Chemistry, Endo.* 10:9–15 (1992). There is need for systems capable of conducting a range of rapid and reliable analyses of a sperm sample.

An object of the invention is to provide analytical systems that can analyze microvolumes of a sperm sample and produce analytical results rapidly. Another object is to provide easily mass produced, disposable, small (e.g., less than 1 cc in volume) devices having mesoscale functional elements capable of rapid, automated analyses of sperm, in a range of applications. It is a further object of the invention to provide a family of such devices that individually can be used to implement a range of rapid tests, e.g., tests for sperm motility, and morphology. Another object is to provide a family of devices for conducting an in vitro fertilization in one device using microvolumes of sample.

SUMMARY OF THE INVENTION

The invention provides methods and apparatus for sperm handling. The devices may be used in a range of applications including sperm motility and morphology testing and in vitro fertilization. In one embodiment, the invention provides a device comprising a solid substrate, typically on the order of a few millimeters thick and approximately a 0.2 to 2.0 centimeters square, microfabricated to define a sample inlet port and a mesoscale channel system. In one embodiment, the device may be used for in vitro fertilization. In this embodiment, the substrate of the device is microfabricated with a sperm inlet port, an egg nesting chamber, and an elongate mesoscale channel communicating between the egg nesting chamber and the inlet port, which permits competitive migration of sperm from the inlet port through the channel to the egg nesting chamber, where fertilization occurs. In another embodiment, the substrate may comprise a sperm inlet port and a mesoscale channel, extending from the inlet port. In this embodiment, sperm may be applied to the inlet port, and the extent of migration of the sperm through the channel can serve as an indicator of sperm motility or morphology. The term "mesoscale" is used herein to define flow passages having cross-sectional dimensions on the order of approximately 0.1 μm to 500 μm, with preferred widths on the order of 2.0 to 300 μm, more preferably 3 to 100 μm. For many applications, channels of 5-50 μm widths will be useful. Chambers in the substrates often will have larger dimensions, e.g., a few millimeters. Preferred depths of channels and chambers are on the order of 0.1 to 100 μm, typically 2-50 μm.

In one embodiment, the mesoscale channel of the device may comprise a fractal region, comprising bifurcations leading to plural secondary channels, to enhance the detection or competitive migration of the sperm sample. The fractal region may comprise, equal numbers of bifurcations and junctions disposed serially along the direction of sperm migration. In one embodiment, the branching channels in the fractal region progressively decrease in cross-sectional area at each bifurcation and increase at each junction. The use of a mesoscale fractal flow channel is disclosed in U.S. Ser. No. 07/877,701, filed May 1, 1992, now abandoned the disclosure of which is incorporated herein by reference. The devices and methods of the invention may be used to implement a variety of automated, sensitive and rapid, contaminant-free tests including clinical analyses of sperm properties and for rapid in vitro fertilization.

Generally, as disclosed herein, the solid substrate comprises a chip containing the mesoscale channel and other functional elements. The channels and elements may be designed and microfabricated from silicon and other solid substrates using established micromachining methods. The chambers and channels in the devices may be microfabricated on the surface of the substrate, and then a cover, e.g., a transparent glass cover, may be adhered, e.g., anodically bonded over the surface. The devices typically are designed on a scale suitable to analyze microvolumes (<10 μL) of sample, introduced into the flow system through an inlet port defined, e.g., by a hole communicating with the flow system through the substrate or cover slip. The volume of the mesoscale channels and chambers typically will be <5 μL, and the volumes of individual channels, chambers, or other functional elements are often less than 1 μL, e.g., in the nanoliter or even picoliter range. Assays can be conducted rapidly and after an assay is complete, the devices can be discarded.

The chips may be used with an appliance which contains a nesting site for holding the chip, and which mates one or more input ports on the chip with one or more flow lines in the appliance. Before or after a sperm sample is applied to the inlet port of the substrate, the chip may be placed in the appliance, and a pump, e.g., in the appliance, can be actuated to introduce a buffer or other fluid to hydraulically fill the channels and chambers or to force the sperm sample or other fluid components into (or out of) the flow system. Alternatively, sperm may be injected into the chip by the appliance. A sperm sample or other fluid component also may enter the channel system simply by capillary action through an inlet port.

The fluid contents of the channels and chambers of the devices may be observed optically, either visually or by machine, through a translucent window, such as a transparent cover over the channel system, or through a translucent section of the substrate itself. Thus, the devices permit the optical detection, e.g., of sperm migration in a channel, or in another embodiment, egg fertilization in an egg nesting chamber. The appliance may comprise means for viewing the contents of the device such as an optical viewing system, such as a microscope or a camera.

In another embodiment, the substrate of the device may include a sperm inlet port, a mesoscale channel extending from the inlet port, and a mesoscale detection chamber in fluid communication with the flow channel. The mesoscale detection chamber is provided with a binding moiety capable of binding with a preselected component of a sperm sample. The detection chamber may be provided, e.g., with a binding moiety capable of detectably binding to a sperm antibody or hormone, to enable the detection of a specific sperm component.

The use of a detection region allows a range of binding assays to be performed on a sperm sample. The use of a mesoscale detection chamber is disclosed in U.S. Ser. No. 07/877,702, filed May 1, 1992, now abandoned.

Some of the features and benefits of devices constructed in accordance with the teachings disclosed herein are summarized in Table 1. A device may include two or more separated systems, e.g., fed by a common inlet port, to .implement a plurality of assays. The device may also comprise a control system so that data from the sample region and the control region may be detected and compared. The devices can be used to implement a range of rapid clinical tests for the analysis of a sperm sample. The devices may be utilized, e.g., for the detection of the motility or morphology of a sperm sample or to test the presence of sperm antibodies or hormones, or to test the interaction of sperm with cervical mucus, or other assays used in infertility testing. In addition, the devices may be utilized to test the interaction of a sperm sample with other reagents such as spermicides. The invention provides methods and devices for use in a wide range of possible assays. Assays may be completed rapidly, and at the conclusion of the assay the chip can be discarded, which advantageously prevents contamination between samples, entombs potentially biologically hazardous material, and provides an inexpensive, microsample analysis.

TABLE 1

| Feature | Benefit |
| --- | --- |
| Flexibility | No limits to the number of chip designs or applications available. |
| Reproducible | Allows reliable, standardized, mass production of chips. |
| Low Cost Production | Allows competitive pricing with existing systems. Disposable nature for single-use processes. |
| Small Size | No bulky instrumentation required. Lends itself to portable units and systems designed for use in non-conventional lab environments. Minimal storage and shipping costs. |
| Microscale | Minimal sample and reagent volumes required. Reduces reagent costs, especially for more expensive, specialized test procedures. Allows simplified instrumentation schemes. |
| Sterility | Chips can be sterilized for use in |

TABLE 1-continued

| Feature | Benefit |
| --- | --- |
|  | microbiological assays and other procedures requiring clean environments. |
| Sealed System | Minimizes biohazards. Ensures process integrity. |
| Multiple Circuit Capabilities | Can perform multiple processes or analyses on a single chip. Allows panel assays. |
| Multiple Detector Capabilities | Expands capabilities for assay and process monitoring to virtually any system. Allows broad range of applications. |
| Reuseable Chips | Reduces per process cost to the user for certain applications. |

BRIEF DESCRIPTION OF THE DRAWINGS

FIG. 1 is a magnified plan view of device 10 according to the invention that comprises substrate 14 microfabricated with ports 16, mesoscale flow channel 20, and a fractally bifurcating system of flow channels 40.

FIG. 2 is a longitudinal cross sectional view of the device shown in FIG. 1.

FIG. 3 is a perspective view of the device of FIG. 1.

FIG. 4 is a schematic cross sectional view of an analytical device 10 nested within an appliance 50, which is used to support the device 10 and to deliver and receive sample fluids to and from device 10.

FIG. 10 is a schematic plan view of an analytical device fabricated with a pair of fractally bifurcating flow channels 40.

Like reference characters in the respective drawn figures indicate corresponding parts.

DETAILED DESCRIPTION

Figure 5:
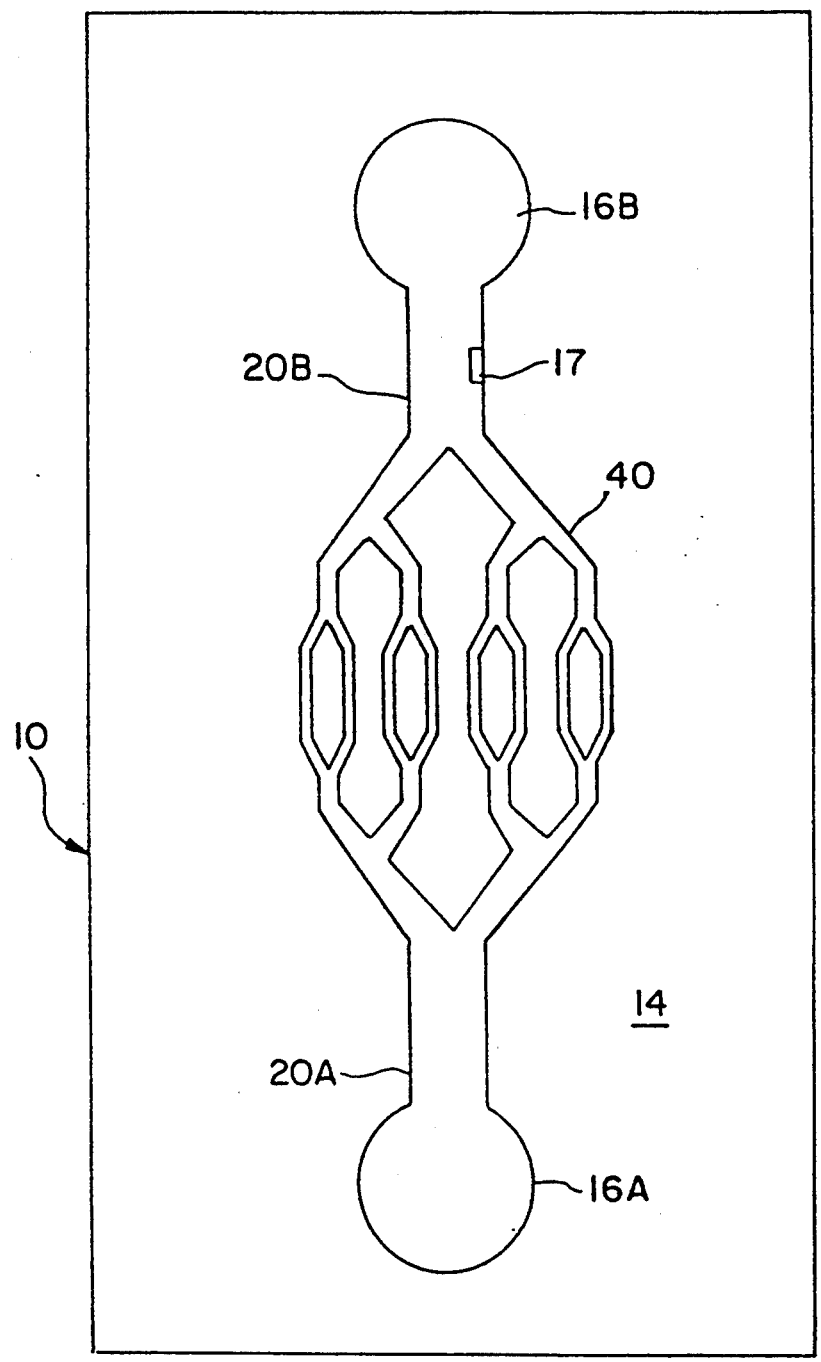
FIG. 5 is a schematic plan view of a substrate 14 microfabricated-with a fractally bifurcating system of flow channels 40 symmetrically disposed on the substrate, and tapering to a narrower diameter towards the center of the fractal system.

The invention provides methods and apparatus for sperm handling, which may be utilized in a range of applications including sperm motility and morphology testing and in vitro fertilization. The invention provides a device comprising a solid substrate, typically on the order of a few millimeters thick and approximately 0.2 to 2.0 centimeters square, microfabricated to define a sperm inlet port and a mesoscale flow system extending from the inlet port. In one embodiment, a sperm sample is applied to the inlet port and the extent of migration of the sperm through the channel can serve as an indication of, e.g., the motility or morphology of the sperm sample. In another embodiment, the substrate may further include an egg nesting chamber, and an elongate channel of mesoscale cross sectional dimension, communicating between the egg nesting chamber and the sperm inlet port. In operation, a sperm sample is applied to the inlet port, and sperm in the sample then migrate competitively through the channel to the egg chamber, where fertilization of the egg occurs.

Analytical devices having mesoscale flow systems can be designed and fabricated in large quantities from a solid substrate material. They can be sterilized easily. Silicon is a preferred substrate material because of the well-developed technology permitting its precise and efficient fabrication, but other materials may be used including cast or molded polymers including polytetrafluoroethylenes. The sample inlet and other ports, the mesoscale flow system, including the flow channel(s) and other functional elements, may be fabricated inexpensively in large quantities from a silicon substrate by any of a variety of micromachining methods known to those skilled in the art. The micromachining methods available include film deposition processes such as spin coating and chemical vapor deposition, laser fabrication or photolithographic techniques such as UV or X-ray processes, or etching methods which may be performed by either wet chemical processes or plasma processes. (See, e.g., Manz et al., *Trends in Analytical Chemistry*, 10:144–149 (1991)).

Flow channels of varying widths and depths can be fabricated with mesoscale dimensions for use in analyzing a sperm sample. The silicon substrate containing a fabricated mesoscale flow channel may be covered and sealed, e.g., anodically bonded, with a thin glass cover. Other clear or opaque cover materials may be used. Alternatively, two silicon substrates can be sandwiched, or a silicon substrate can be sandwiched between two glass covers. The use of a transparent cover results in a window which facilitates dynamic viewing of the channel contents, and allows optical probing of the mesoscale flow system either visually or by machine. Other fabrication approaches may be used.

The capacity of the devices is very small and therefore the amount of sample fluid required for an analysis is low. For example, in a 1 cm×1 cm silicon substrate, having on its surface an array of to 100500 grooves which are 10 microns wide ×10 microns deep ×1 cm ($10^4$ microns) long, the volume of each groove is $10^{-3}$ μL and the total volume of the 500 grooves is 0.5 μL. The low volume of the mesoscale flow systems allows assays to be performed on very small amounts of a liquid sample (<5 μL). The mesoscale devices may be microfabricated with microliter volumes, or alternatively nanoliter volumes or less, which advantageously limits the amount of sample, buffer or other fluids required for an analysis. Thus, an important consequence and advantage of employing flow channels having mesoscale dimensions is that very small scale analyses can be performed.

In one embodiment, illustrated schematically in FIGS. 1, 2 and 3, the device 10 may be utilized for a rapid assay of, e.g., the motility or morphology of a sperm sample. Device 10 includes a silicon substrate 14 microfabricated with ports 16, primary sample channel 20A, and a fractal system of channels 40. The ports may be microfabricated with mesoscale or larger dimensions. The fractal region 40 in this case comprises equal numbers of bifurcations and junctions, disposed serially through the fractal region, leading to a third channel 20B. The substrate 14 is covered with a clear glass or plastic window 12 to form an enclosing wall of the channels. In operation, after hydraulically filling all channels with an appropriate liquid medium, e.g., cervical mucus or a buffer, a sperm sample is applied at inlet port 16A. Sperm in the sample migrate into flow channel 20A, and then through the fractal region 40 towards channel 20B and port 16B. The extent of progress of a sperm sample through the fractal path 40 can serve as an indicator of sperm motility and morphology. The flow of a sperm sample may be detected optically, e.g., with a microscope, either visually or by machine, through the transparent cover over the flow system, or through a transparent region of the substrate itself.

In another embodiment, the fractal system 40 may be microfabricated on a silicon substrate with reduced dimensions at each bifurcation, providing sequentially narrower flow channels, as illustrated schematically in FIG. 5. FIG. 5 shows device 10, which comprises substrate 14 microfabricated with fractal flow channels 40, which have a reduced cross-sectional area relative to the primary flow channel 20A and the third flow channel 20B. In operation, sperm in a sample enter device 10 through inlet port 16A and channel 20A, and migrate through the fractal region 40 towards channel 20B and port 16B. The fractal region 40 provides an extensive network suitable for the competitive migration of a sperm sample. The fractal system may be microfabricated with a more complex series of bifurcations, as illustrated schematically in device 10 in FIG. 10, which includes a pair of fractally bifurcating channels 40A and 40B. The fractal channel network 40A is constructed with sequentially narrower channels towards the center of the fractal, thereby enhancing sensitivity to sperm migration.

The analytical devices containing the mesoscale channel system can be used in combination with an appliance for delivering and receiving fluids to and from the devices, such as appliance 50 shown schematically in FIG. 4, which incorporates a nesting site 58 for holding the device 10, and for registering ports, e.g., ports 16 on the device 10, with a flow line 56 in the appliance. The appliance also includes pump 52 which may be used to inject or receive sample fluids into or from device 10. Alternatively, the sample may be injected into the device, or may enter the flow system simply by capillary action. Devices such as valves and other mechanical sensors for detecting sample fluid in the devices can be fabricated directly on the silicon substrate and can be mass-produced according to well established technologies. Angell et al., *Scientific American*, 248:44–55 (1983). Alternatively, sensors such as optical detectors and other detection means may be provided in the appliance utilized in combination with the device.

Figure 12:
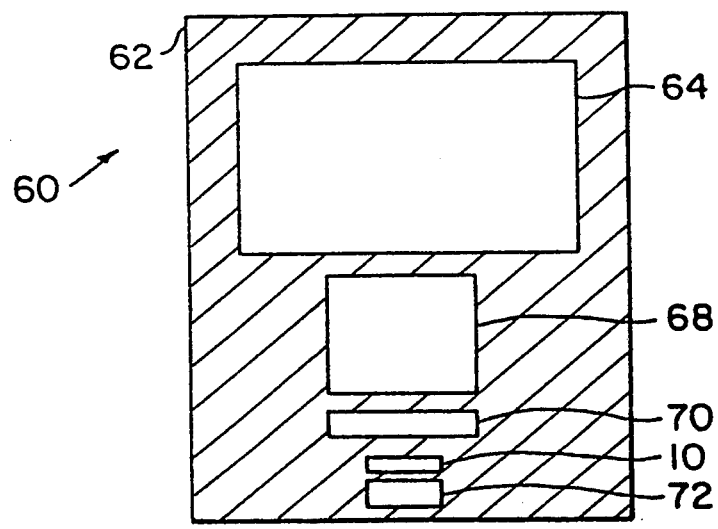
FIG. 12 is a schematic cross sectional view of the apparatus 60 of FIG. 11.
Figure 11:
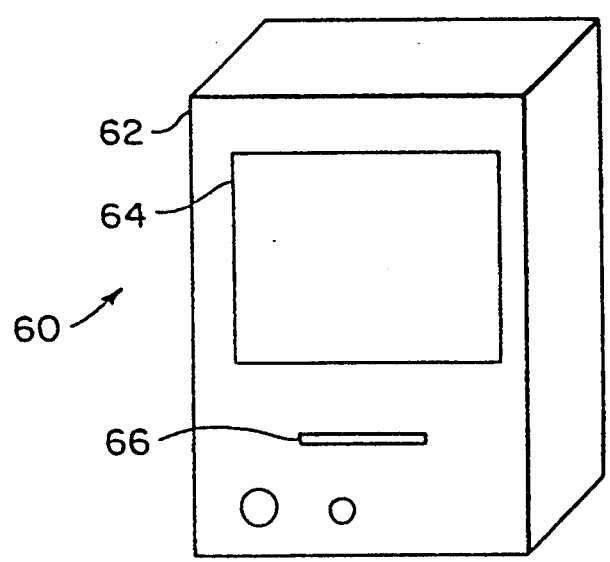
FIG. 11 is a schematic perspective view of an apparatus 60 used in combination with device 10 for viewing the contents of device 10.

In one embodiment, the analytical devices also may be utilized in combination with an appliance for viewing the contents of the devices.. The appliance may comprise a microscope for viewing the contents of the chambers and channels in the devices. In another embodiment, a camera may be included in the appliance, as illustrated in the appliance 60 shown schematically in FIGS. 11 and 12. The appliance 60 is provided with a housing 62, a viewing screen 64 and a slot 66 for inserting a chip into the appliance.. As shown in cross section in FIG. 12, the appliance 60 may also include a video camera 68, an optical system 70, and a tilt mechanism 72 for holding device 10, and allowing the placement and angle of device 10 to be adjusted manually. The ,optical system 70 may include a lens system for magnifying the channel contents, as well as a light source. The video camera 68 and screen 64 allow sample fluids to be monitored visually, and optionally to be recorded using the appliance.

Figure 8:
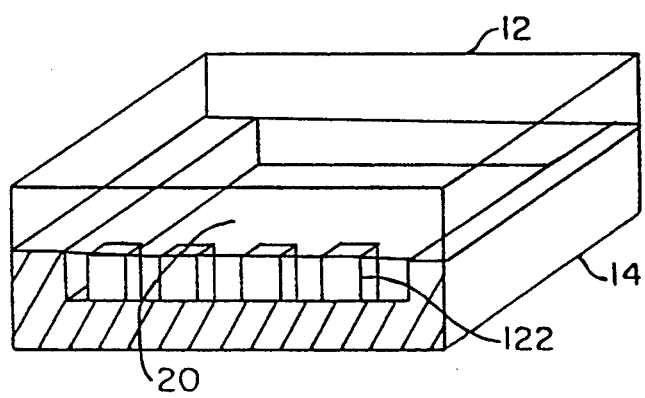
FIG. 8 is a cross sectional perspective view of flow channel 20 on an inert substrate 14, with protrusions 122 extending from a wall of the flow channel, which serve as a barrier to the migration of sperm.

In another embodiment, the substrate may be disposed, e.g., in an appliance, at an angle with respect to a horizontal plane, to provide an incline for the travel of a sperm sample, to further enhance the detection of motility. In another embodiment, the sperm flow channel may comprise protrusions 122, illustrated in FIG. 8, to provide a barrier for competitive migration of sperm.

The devices may be microfabricated with a mesoscale flow channel that includes a detection region for detecting a component of a sperm sample, such as sperm antibodies or hormones. The detection region may comprise a binding moiety, capable of binding to a predetermined component of the sperm sample. The binding moiety, such as an antigen binding protein, may be immobilized on the surface of the flow channels, or on a solid phase reactant such as a bead. The binding moiety in the detection region may be introduced into the detection region in solution, or alternatively, may be immobilized on the surface of the mesoscale flow channels by, e.g., physical absorption onto the channel surfaces, or by chemical activation of the surface and subsequent attachment of biomolecules to the activated surface. Techniques available in the art may be utilized for the chemical activation of silaceous channel surfaces, and for the subsequent attachment of a binding moiety to the surfaces. (See, e.g., Hallet in: *Solid Phase Biochemistry*, W. H. Scouten, Ed., John Wiley, New York, pp 535–597 (1983); and Mandenius et al., *Anal. Biochem.*, 137:106–114 (1984), and *Anal. Biochem.*, 170:68–72 (1988)). The use of a binding moiety for assays in a mesoscale detection chamber, as well as techniques for providing the binding moiety in the detection chamber, are disclosed in the related application, U.S. Ser. No. 07/877,702, filed May, 1, 1992, now abandoned. The detection chamber may be utilized in a range of binding assays, e.g., to assay the interaction of a sperm sample with cervical mucus, to test the efficacy of spermicides, to assay for the presence of antibodies or contaminants in the sample, or to conduct sperm counts.

Figure 6:
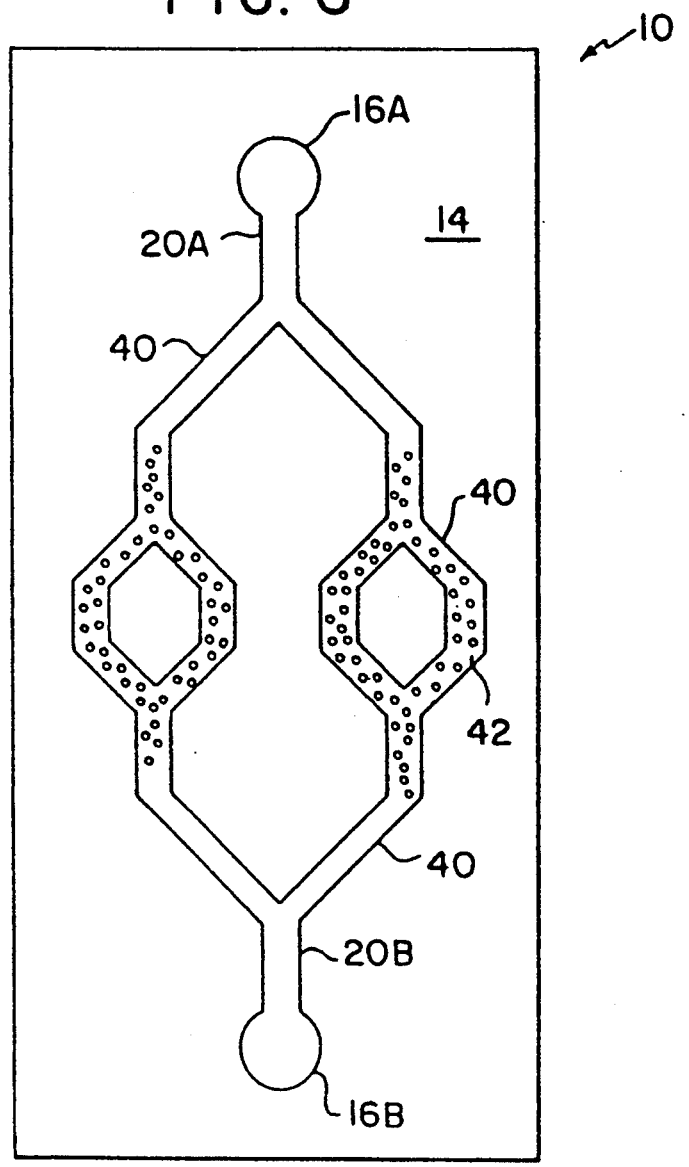
FIG. 6 is a schematic plan view of device 10 that includes substrate 14 microfabricated with a fractally bifurcating system of flow channels 40, provided with beads 42 to enhance flow restriction and agglomeration in the fractal.

In one embodiment, the binding moiety may be immobilized on a particle capable of inducing detectable agglomeration of a component of a sperm sample in a fractal mesoscale flow system. As illustrated in device 10, shown schematically in FIG. 6, particles 42, coated with binding protein specific for a given analyte in the sperm sample, may be provided in the fractal region 40 to promote analyte-induced agglomeration of fluid in the fractal region. Agglomeration in the fractal region may be detected optically through a window, e.g., disposed over the fractal region, or, e.g., by detecting pressure or conductivity changes of the sample fluid.

Figure 7:
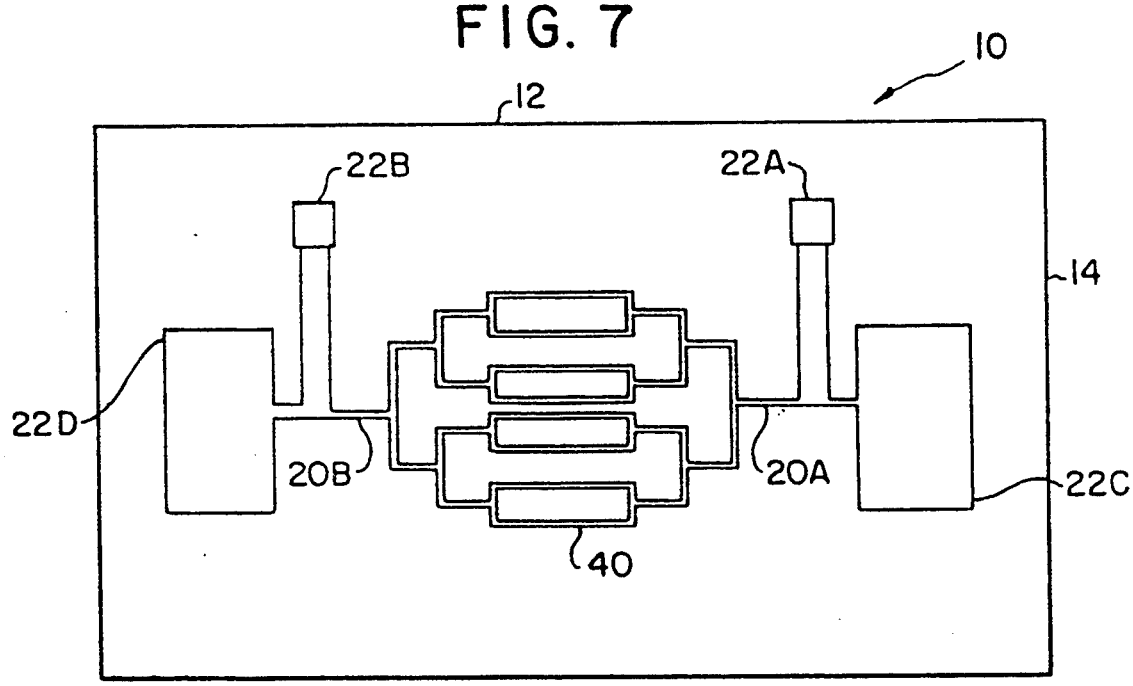
FIG. 7 is a magnified plan view of a device 10 which includes a sperm chamber 22C and an egg nesting chamber 22D which are connected by the fractal flow system 40.

In another embodiment, the devices of the invention may be utilized to conduct an in vitro fertilization. One embodiment of an in vitro fertilization device is shown in FIG. 7. Device 10 in FIG. 7 includes a sperm chamber 22C and an egg nesting chamber 22D, connected by a mesoscale fractal channel system 40. The device includes a clear cover 12, which is disposed over the fractal region and partly across the top of chambers 22C and 22D, leaving an open port at the top of the chambers. Alternatively, the cover 12 may extend over the entirety of the surface (not shown), and define holes disposed over the chamber 22C and 22D, which permit introduction of sperm and egg, but discourage evaporation. In operation, a sperm sample is applied to chamber 22C, e.g., through the top of the chamber. An egg is placed in the nesting chamber 22D. The flow system including chambers 22C and 22D, channels 20 and the fractal region 40, are provided with a buffer including, e.g., mammalian tubal fluid. The flow system also can include the buffer chambers 22B and 22A, in fluid communication with the flow system, which are filled with buffer to alleviate the potentially destructive effects of fluid loss from evaporation or dehydration from within the substrate. Competitive migration of the sperm sample from chamber 22C occurs through the fractal region 40 to the egg nesting chamber 22D where fertilization of the egg occurs. Fertilization can be determined, e.g., optically, either visually or by machine, by observing early stages of egg cell division. The device may be utilized in combination with an appliance mated to ports in the device for the addition or withdrawal of fluid components from the device. The appliance may include, e.g., means, such as a pump or syringe, for hydraulically expelling a fertilized egg from the device subsequent to fertilization, e.g., directly into a host uterus, e.g., by forcing saline or other liquid through the channels.

Figure 13:
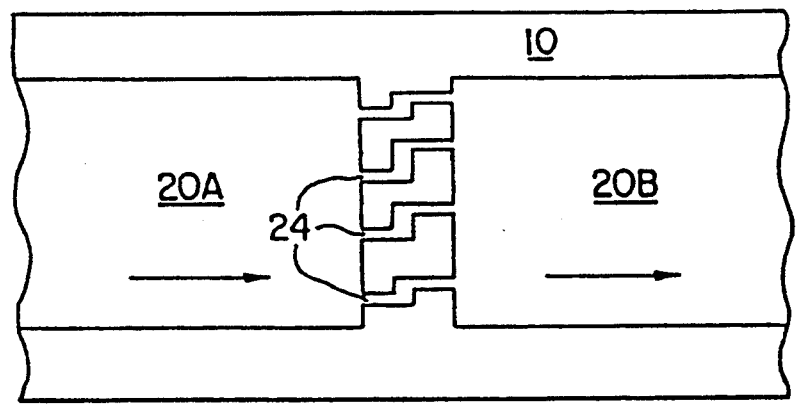
FIG. 13, 14 and 15 illustrate top plan views of magnified different embodiments of a mesoscale filter microfabricated in a flow channel 20 in an analytical device 10.
Figure 14:
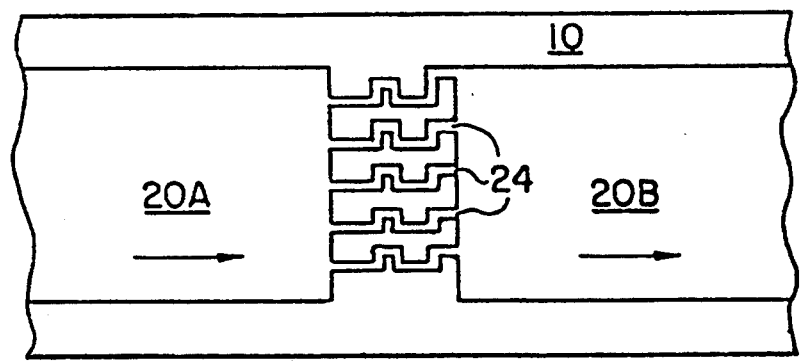
Figure 15:
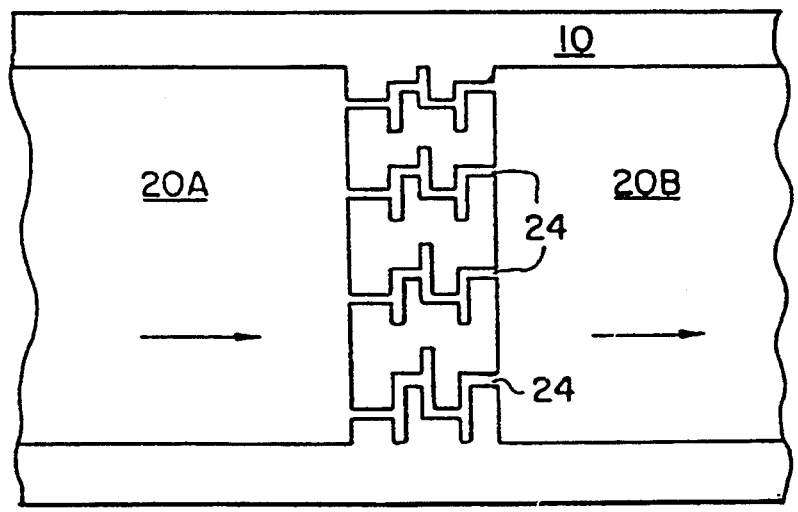

The mesoscale channel system may be microfabricated with a a filter for filtering sperm sample components. The filter may be microfabricated in the flow system between the sperm inlet port and the egg nesting region to enable the filtration of the sample. Filters which may be microfabricated in the flow system include the filters 24 shown in FIGS. 13, 14 and 15. In the device 10, the Filter 24 is microfabricated between the flow channels 20A and 20B allowing sample fluid in channel 20A to pass through the filter 24. The filtrate exits through the filter 24 into channel 20B. Filter 24 comprises mesoscale flow channels of reduced diameter in comparison with channel 20A–20B, microfabricated with depths and widths on the order of 0.1 to 20 $\mu m$. In contrast, the flow channels 20A and 20B have widths on the order of a maximum of approximately 500 $\mu m$ and more typically 100 $\mu m$. Other filter means may be utilized, such as the posts 122 extending from a wall of the flow channel 20 shown in FIG. 8.

The devices may be used to implement a variety of automated, sensitive and rapid clinical analyses of a sperm sample. The devices can be used in a range of applications including fertility tests of a sperm sample, tests of sperm binding properties, in vitro fertilization, and forensic analyses. In order to enhance the accuracy of an assay, the substrate may be fabricated to include a control region in the flow system, e.g., a region which is identical in geometry to the test region, but does not include binding moieties. Sample fluid is directed to both the analytical and control regions to allow the comparison of the regions. The devices also may comprise a plurality of mesoscale flow systems to enable a plurality of assays to be conducted on a sperm sample. At the conclusion of the assay the devices typically are discarded. The use of disposable devices eliminates contamination among samples. The sample at all times can remain entombed, and the low volume simplifies waste disposal.

The invention will be understood further from the following nonlimiting examples.

EXAMPLE 1

Sperm motility is tested in the chip 10 shown schematically in FIG. 5. A sample of semen (<2 $\mu L$) is placed on a glass microscope slide, and the chip 10 is placed on top of the semen sample such that the port 16A is positioned on the semen sample. The progress of individual spermatozoa into port 16A, through channel 20A and fractal region 40 is monitored using a microscope. The experimental results may be compared with results previously established for a healthy sperm sample to provide a test of sperm motility.

EXAMPLE 2

A channel containing a barrier 122 with 7 $\mu m$ gaps (illustrated in cross section in FIG. 8) is filled with HTF-BSA medium and a semen sample applied at the entry hole. The progression of the sperm through the barrier serves as an indicator of sperm motility.

EXAMPLE 3

Figure 9:
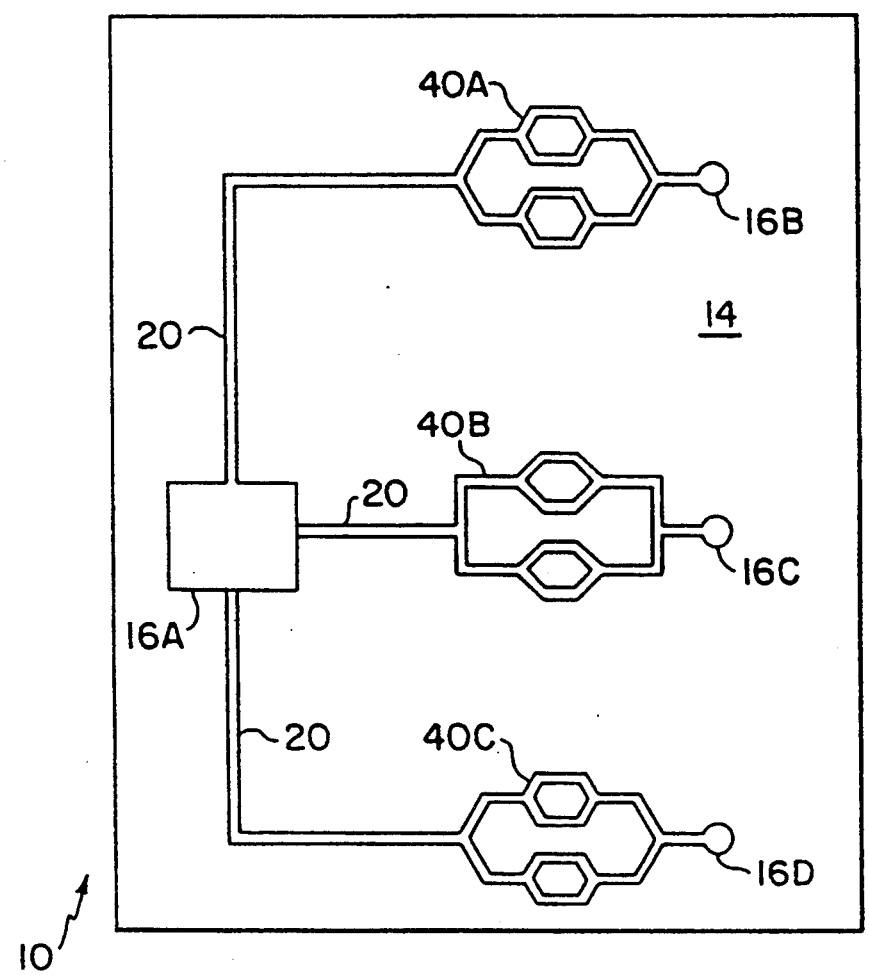
FIG. 9 is a schematic plan view of a multitest apparatus constructed in accordance with the invention.

Sperm functions are tested on the microfabricated solid substrate 14 shown in FIG. 9. A sperm sample is added to the inlet port 16A and then flows through the mesoscale flow channel 20 to the detection chambers 40A, 40B and 40C. Fractal detection chamber 40A provides a test for leucocytes and comprises immobilized antibody to common leukocyte antigen. Fractal detection chamber 40B provides a test for sperm antibodies and contains immobilized antibody to human IgG, IgA or IgM. Fractal detection chamber 40C provides a test for acrosome reaction and contains fluorescein labeled lectin. Flow restriction due to agglutination in the chambers may be detected, e.g., by optical detection through a glass cover disposed over the substrate. After the assay is complete, the device is discarded.

EXAMPLE 4

A chip of tile type illustrated in FIG. 7, defining an egg nesting chamber and a sperm inlet port, connected by a mesoscale channel, was washed with ultra-pure water and then filled with HTF-BSA. Eggs and semen were harvested from appropriate donors. A single egg was transferred to the egg nesting chamber using a micropipette, and a sample of semen was applied to the sperm inlet port using a micropipette. This entire procedure was conducted under a laminar flow hood and the application of the egg and semen was confirmed visually using a microscope. Progression (and selection of sperm) through the flow channel connecting the sperm inlet port and the egg nesting chamber containing the egg was confirmed visually. The chip was placed in a moist environment to minimize evaporation from the chip, and then incubated at 37° C. for several hours. Fertilization of the egg was confirmed by visual inspection. Implantation of the fertilized egg was achieved by expelling the entire contents of the chip. Additionally, the chip contains a reservoir of HTF-BSA in connection with the chambers and flow channel in order to compensate for any evaporation from the chip.

EXAMPLE 5

Experiments were performed in mesoscale flow channels testing the sperm motility of human semen samples. In a sperm motility test, microchannels (80 μm wide, 20 μm deep, and 10 mm long) in a glass-silicon chip were filled with Human Tubal Fluid (HTF) medium (Irvine Scientific, Santa Aria, Calif.) containing 0.5% BSA (HTF-BSA). A sample of semen (<2 μL) was placed on a glass microscope slide and the chip placed on top of the semen sample such that the entrance to the channel was positioned on the semen sample. The progress of individual spermatozoa into the channel and along its length to the exit hole was monitored using a microscope, and recorded using a TV camera and video recorder. Spell were observed traversing the entire length of the channel and could be seen accumulating in the exit hole. Migration of sperm was also demonstrated in channels of 40, 100, and 120 μm depths.

Sperm motility in fractal channels also was determined, by examining the distance the sperm traveled along the fractal flow path. The above experiment was repeated using a fractal channel (40 μm wide, 20 μm deep) filled with HTF-BSA medium. Sperm were observed migrating through the tortuous fractal pathway (a total of 9 right angle turns, e.g., the device of FIG. 11) from the entry to the center of the channel. The experiment was repeated using a fractal channel which was 20 μm deep, but which was reduced in width at each bifurcation (40, 30, 25, 20, and 10 μm) and then increased in width (20, 25, 30, 40 μm). Again sperm migrated to the center of the fractal channel.

The bi-directional motility of a sperm sample was also examined. A channel (60 and 80 μm wide, 20 μm deep) and fractal channels were filled with HTF-BSA medium and semen introduced simultaneously via the holes at each end of the channel. Sperm were observed migrating towards the center of the channel (or fractal channel) and eventually passing as they migrated towards the hole at the opposite end of the channel.

An inclined channel experiment was also performed on a sperm sample. A channel (60 μm wide, 20 μm deep) was filled with HTF-BSA medium and a sample of sperm applied to the inlet hole. The inlet and outlet holes were sealed with adhesive tape. The chip was inclined at 45° for different periods of time and then the progression of the sperm up the channel determined visually. Sperm were found to migrate efficiently up the inclined channel and could be seen in the exit hole at the top of the channel.

EXAMPLE 6

An experiment testing different spermicides using a mesoscale flow system was conducted. A chip comprising two chambers (5.2 mm long, 750 μm wide, 1.5 mm deep) each linked at each end to an entry hole by a channel (3.25 mm long, 100 μm wide, 20 μm deep) was used for the simultaneous testing of the spermicidal activity of nonoxynol-9 and C13-G (Biosyn, Inc., Pa.). The four channels were filled with HTF-BSA solution (channel #1, control), 0.005% (channel #2), 0.0125% (channel #3), and 0.05% (channel #4) nonoxynol-9 (or C13-G), respectively. A sample of semen was placed in each chamber and the progress of sperm into the adjoining channels monitored using the microscope. The number of sperm observed in the channels was in the following order of decreasing sperm count: channel #1 > #2 > #3 > #4. Most sperm were seen in the control channel, and none were seen in channel #4 which contained nonoxynol-9 or C13G at the optimum concentration for spermicidal action.

EXAMPLE 7

A morphological examination of motile sperm was conducted in a mesoscale flow system. A chip comprising two chambers (5.2 mm long, 750 μm wide, 1.5 mm deep) each linked at each end to an entry hole by a channel (3.25 mm long, 100 μm wide, 20 μm deep) was used. The channels were filled with HTF-BSA solution and a semen sample applied to the central chamber. The chip was placed in a moist environment for 10 minutes. The surface solution from the holes at each end of the chip was removed and placed on a glass microscope slide (previously washed with ethanol). The slide was dried at 40° C. then stained using Wright Giemsa stain (Curtin Matheson Scientific, Inc., Houston, Tex.). The sperm which had migrated from the central chamber to the end of the channel and into the hole had a normal morphological appearance.

EXAMPLE 8

The interaction of a sperm sample with cervical mucus in a mesoscale flow system was tested in a chip comprising two chambers (5.2 mm long, 750 μm wide, 1.5 mm deep) each linked at each end to an entry hole by a channel (3.25 mm long, 100 μm wide, 20 μm deep). The channels were filled with HTF-BSA solution and a cervical mucus sample (collected at approximately day 14 of the patient's menstrual cycle) placed in each of the central chambers. Sperm did not migrate into the cervical mucus and those that penetrated died, as anticipated because cervical mucus is known to be hostile to sperm at this time during the menstrual cycle. Moghissi et al., *Am. J. Obstet. Gynecol.*, 114:405 (1972).

EXAMPLE 9

A test of the interaction of hyaluronic acid with a sperm sample was conducted to assess the cervical interaction of a sperm sample. The test was conducted in a chip comprising two chambers (5.2 mm long, 750 μm wide, 1.5 mm deep) each linked at each end to an entry hole by mesoscale flow Channels #1, #2, #3 and #4 (3.25 nun long, 100 μm wide, 20 μm deep). Channel #1 was a control channel. Channels were filled with HTF-BSA solution and solutions of hyaluronic acid (Sigma) in HTF-BSA (channels #2, #3, #4, 5 mg/mL, 2.5 mg/mL, and 1.3 mg/mL, respectively). A semen sample was placed in each of the central chambers. Sperm did not migrate into channel #2, containing 5 mg/mL hyaluronic acid, but the extent of migration increased as the concentration of hyaluronic acid decreased in channels #3 and #4.

EXAMPLE 10

An immunobead test for the presence of IgG antibodies in a sperm sample was conducted. Immunobeads (BioRAD, Richmond, Calif.), microbeads coated with an antibody to human IgG, were diluted to 1 mg/mL in HTF-BSA solution (Irvine Scientific, Santa Ana, Calif.). A microchannel (250 μm wide, 20 μm deep, and 10 mm long) in a glass-silicon chip was filled with a sample of the immunobead solution and a semen sample (ca 1.2 μL) was applied to the channel entry. Agglutination of sperm by the immunobeads due to the presence of antibodies in the sperm sample was observed in the channel. As a control, the experiment was performed on a glass microscope slide using larger volumes of the immunobead reagent and semen sample, and this was also positive (agglutination observed).

It will be understood that the above descriptions are made by way of illustration, and that the invention may take other forms within the spirit of the structures and methods described herein. Variations and modifications will occur to those skilled in the art, and all such variations and modifications are considered to be part of the invention, as defined in the claims.

What is claimed is:

1. A device for the in vitro fertilization of an egg, the device comprising:
    a solid substrate microfabricated to define:
        a plurality of flow systems, each said flow system comprising:
            an egg nesting chamber;
            a sperm inlet port; and
            an elongate channel of mesoscale cross-sectional dimension, communicating between said egg nesting chamber and said sperm inlet port, which permits competitive sperm migration from said inlet port to said nesting chamber for egg fertilization; and
        an egg disposed within each said nesting chamber.

2. A device for the in vitro fertilization of an egg, the device comprising:
    a solid substrate microfabricated to define:
        a plurality of egg nesting chambers;
        a sperm inlet port; and
        a plurality of elongate channels, each said channel being of mesoscale cross-sectional dimension, and each said channel communicating between said sperm inlet port and one of said egg nesting chambers, thereby to permit competitive sperm migration from said inlet port through each said channel to each said nesting chamber for egg fertilization; and
        an egg disposed within each said nesting chamber.

* * * * *

UNITED STATES PATENT AND TRADEMARK OFFICE
CERTIFICATE OF CORRECTION

PATENT NO. : 5,427,946
DATED : June 27, 1995
INVENTOR(S) : Larry J. Kricka, et al It is certified that error appears in the above-indentified patent and that said Letters Patent is hereby corrected as shown below:

On the title page, item [*] Notice should read --The portion of the term of this patent subsequent to May 1, 2012 has been disclaimed--.

Signed and Sealed this

Twelfth Day of March, 1996

Attest:

BRUCE LEHMAN

Attesting Officer   Commissioner of Patents and Trademarks